United States Patent
Grela et al.

(10) Patent No.: US 8,318,965 B2
(45) Date of Patent: Nov. 27, 2012

(54) COMPLEX OF RUTHENIUM, METHOD OF PRODUCTION THEREOF AND USE THEREOF AS (PRE)CATALYSTS OF THE METATHESIS REACTION

(75) Inventors: Karol Grela, Warsaw (PL); Michal Barbasiewicz, Warsaw (PL); Anna Szadkowska, Warsaw (PL)

(73) Assignee: UMICORE AG & Co. KG, Hanau-Wolfgang (DE)

( * ) Notice: Subject to any disclaimer, the term of this patent is extended or adjusted under 35 U.S.C. 154(b) by 529 days.

(21) Appl. No.: 12/303,615

(22) PCT Filed: Jun. 1, 2007

(86) PCT No.: PCT/EP2007/004901
§ 371 (c)(1), (2), (4) Date: Apr. 3, 2009

(87) PCT Pub. No.: WO2007/140954
PCT Pub. Date: Dec. 13, 2007

(65) Prior Publication Data
US 2010/0174068 A1    Jul. 8, 2010

(30) Foreign Application Priority Data
Jun. 7, 2006 (PL) .......................... 379879

(51) Int. Cl.
*C07F 15/00* (2006.01)
(52) U.S. Cl. ........................ 556/137; 546/152
(58) Field of Classification Search .............. 546/152; 556/137
See application file for complete search history.

(56) References Cited

FOREIGN PATENT DOCUMENTS
WO    2004/035596 A    4/2004

OTHER PUBLICATIONS

Szadkowska, A. et al.: "Synthesis and application of new latent ruthenium carbene catalysts" European Congress of Young Chemists "Youngchem 2005" (Poster), [Online] 2005, XP002455275, Rydzyna, Poland, retrieved from the Internet: URL:http://zinc.ichf.edu.pl/pubs/b32/poster_Ania_Szadkowska.pdf> [retrieved on Oct. 17, 2007].

Slugovc, C. et al.: "Thermally switchable olefin metathesis initiators bearing chelating carbenes: influence of the chelate's ring size" Organometallics, vol. 24, 2005, pp. 2255-2258, XP002455276.

Ung, T. et al.: "Latent Ruthenium olefin metathesis catalysts that contain an N-heterocyclic carbene ligand" Organometallics, vol. 23, 2004, pp. 5399-5401, XP002455277.

Barbasiewicz, Michal et al: "Structure and Activity Peculiarities of Ruthenium Quinoline and Quinoxaline Complexes: Novel Metathesis Catalysts" Organometallics, 25(15), 3599-3604 Coden: ORGND7; ISSN: 0276-7333, Jun. 17, 2006, XP002455278.

International Search Report, PCT/EP2007/004901, mailed Nov. 7, 2007.

International Written Opinion, PCT/EP2007/004901, mailed Nov. 7, 2007.

*Primary Examiner* — Douglas M Willis
(74) *Attorney, Agent, or Firm* — Levin Santalone LLP; John Santalone

(57) ABSTRACT

The present invention provides ruthenium compounds of the formula

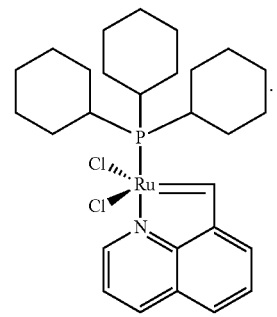

The compounds of the invention occur in the form of two isomers: trans and cis. The method of production of the compounds according to the invention is based on reacting an intermediate of formula (5) with a carbene complex of ruthenium. The invention also relates to the use of the compounds according to the invention for carrying out metathesis reactions.

7 Claims, 1 Drawing Sheet

COMPLEX OF RUTHENIUM, METHOD OF PRODUCTION THEREOF AND USE THEREOF AS (PRE)CATALYSTS OF THE METATHESIS REACTION

BACKGROUND OF THE INVENTION

The invention relates to novel metal complexes with formula 1, where

M denotes ruthenium or osmium,

L denotes a neutral ligand, selected from the group comprising amines, imines, phosphines (preferably stilbines, arsines, alcohols, thiols, ethers and thioethers or the N-heterocyclic carbene ligand (NHC) represented by formula 9, where B denotes the methylene (—C—), 1,2-ethylene (—C—C—), 1,3-propenyl (—C—C—C—), 1,2-ethenylene (—C=C—) or azaethenyl (—N=C—) residue, unsubstituted or substituted with halogens, $C_5$-$C_{24}$ aryl, $C_1$-$C_6$ alkyl, $C_1$-$C_{13}$ perfluoroalkyl, $C_1$-$C_6$ cycloalkyl groups, moreover the alkyl groups may be joined together in a ring; preferably B denotes 1,2-ethylene (—$CH_2$—$CH_2$—)

R and R' denote, independently of one another, $C_5$-$C_{24}$ aryl, $C_5$-$C_{24}$ perfluoroaryl, $C_1$-$C_{26}$ alkyl, $C_1$-$C_{26}$ perfluoroalkyl, $C_1$-$C_7$ cycloalkyl groups, unsubstituted or substituted with halogens, $C_5$-$C_{24}$ aryl, $C_1$-$C_6$ alkyl, $C_1$-$C_{13}$ perfluoroalkyl, $C_1$-$C_6$ cycloalkyl groups, moreover the alkyl groups may be joined together in a ring, preferably R and R' denote, independently of one another, phenyl groups substituted with $C_1$-$C_{26}$ alkyl residues, most preferably 2,4,6-trimethylphenyl X and X' denote an anionic ligand, selected independently of one another from the group comprising anions of halogens, the phenolate anion ($C_6H_5O^-$) and perfluorophenolate anion ($C_6F_5O^-$), residues of arylcarboxylic, alkylcarboxylic, perfluoroalkylcarboxylic, alkylsulphonic, arylsulphonic, perfluoroalkylsulphonic acids, preferably chlorine $R^1$ denotes hydrogen, $C_1$-$C_5$ alkyl, $C_2$-$C_5$ alkene or $C_3$-$C_7$ cycloalkyl, preferably hydrogen $R^2$, $R^3$, $R^4$, $R^5$, $R^6$, $R^7$ denote, independently, $C_1$-$C_{25}$ alkyl, $C_1$-$C_{25}$ perfluoroalkyl, $C_5$-$C_{24}$ aryl, $C_2$-$C_{25}$ alkene or $C_3$-$C_7$ cycloalkyl, the nitro (—$NO_2$), cyano (—CN), carboxyl (—COOH), ester (—COOR"), sulphone (—$SO_2$R"), formyl (—CHO), sulphonamide (—$SO_2NR"_2$), or ketone (—COR") group, in which groups R" has the following meaning: $C_1$-$C_5$ alkyl, $C_1$-$C_5$ perfluoroalkyl, $C_5$-$C_{24}$ aryl, A denotes either nitrogen or carbon placed with an $R^5$ group having the meaning given above and a method of production thereof.

Compounds of formula 1 occur as two isomers: with formula 1a, in which atoms X and X' are arranged trans relative to one another (see for example FIG. 1), and with formula 1b, in which atoms X and X' are arranged cis relative to one another (see for example FIG. 2). The invention also relates to the use of the compounds of formula 1, both as the pure isomers with formula 1a and with formula 1b and of mixtures thereof, as (pre)catalysts in processes of metathesis.

In applications of metathesis of olefins in organic synthesis, much progress has been achieved in recent years especially in the fields of organic chemistry and polymer chemistry. Practical applications, especially on an industrial scale, require these complexes to be stable for a prolonged time in conditions of elevated temperature and it should be possible to store, transport and use them without a protective gas atmosphere. Rapidly initiating (pre)catalysts, for example of formula 2, in which Mes denotes 2,4,6-trimethylphenyl, are often characterized by lower thermal stability. In addition, some metathesis reactions, especially polymerizations (ROMP, ADMET), are difficult to control in the case of rapidly initiating (pre)catalysts. For this reason it may be advantageous to use (pre)catalysts that are characterized by a lower rate of initiation of the metathesis reaction and that possess high thermal and chemical stability (Organometallics 2005, 24, 2255). This group of (pre)catalysts has found application in particular in polymer chemistry, as initiators permitting controlled polymerization. Representatives of such (pre)catalysts are the pyridine derivatives represented by formula 3, in which iPr denotes isopropyl (Journal of Organometallic Chemistry 2000, 606, 65) and 4 (Organometallics 2004, 23, 5399).

It was found, unexpectedly, that the novel complexes of ruthenium and osmium according to the invention represented by formula 1 are particularly advantageous as (pre) catalysts, they display a low rate of initiation in ring-closure metathesis, and permit a controlled reaction of polymerization by ring opening, while displaying unusually high thermal stability and resistance to oxygen and moisture.

SUMMARY OF THE INVENTION

The complexes of ruthenium and osmium according to the invention are represented by formula 1, in which:

M denotes ruthenium or osmium,

L denotes a neutral ligand, selected from the group comprising amines, imines, phosphines (preferably stilbines, arsines, alcohols, thiols, ethers and thioethers or the N-heterocyclic carbene ligand (NHC) represented by formula 9, where B denotes the methylene (—C—), 1,2-ethylene (—C—C—), 1,3-propenyl (—C—C—C—), 1,2-ethenylene (—C=C—) or azaethenyl (—N=C—) residue, unsubstituted or substituted with halogens, $C_5$-$C_{24}$ aryl, $C_1$-$C_6$ alkyl, $C_1$-$C_{13}$ perfluoroalkyl, $C_1$-$C_6$ cycloalkyl groups, moreover the alkyl groups may be joined together in a ring; preferably B denotes 1,2-ethylene (—$CH_2$—$CH_2$—)

R and R' denote, independently of one another, $C_5$-$C_{24}$ aryl, $C_5$-$C_{24}$ perfluoroaryl, $C_1$-$C_{26}$ alkyl, $C_1$-$C_{26}$ perfluoroalkyl, $C_1$-$C_7$ cycloalkyl groups, unsubstituted or substituted with halogens, $C_5$-$C_{24}$ aryl, $C_1$-$C_6$ alkyl, $C_1$-$C_{13}$ perfluoroalkyl, $C_1$-$C_6$ cycloalkyl groups, moreover the alkyl groups may be joined together in a ring, preferably R and R' denote, independently of one another, phenyl groups substituted with $C_1$-$C_{26}$ alkyl residues, most preferably 2,4,6-trimethylphenyl X and X' denote an anionic ligand, selected independently of one another from the group comprising anions of halogens, the phenolate anion ($C_6H_5O^-$) and perfluorophenolate anion ($C_6F_5O^-$), residues of arylcarboxylic, alkylcarboxylic, perfluoroalkylcarboxylic, alkylsulphonic , arylsulphonic, perfluoroalkylsulphonic acids, preferably chlorine $R^1$ denotes hydrogen, $C_1$-$C_5$ alkyl, $C_2$-$C_5$ alkene or $C_3$-$C_7$ cycloalkyl, preferably hydrogen $R^2$, $R^3$, $R^4$, $R^5$, $R^6$, $R^7$, denote, independently, $C_1$-$C_{25}$ alkyl, $C_1$-$C_{25}$ perfluoroalkyl, $C_5$-$C_{24}$ aryl, $C_2$-$C_{25}$ alkene or $C_3$-$C_7$ cycloalkyl, the nitro (—$NO_2$), cyano (—CN), carboxyl (—COOH), ester (—COOR"), sulphone (—$SO_2$R"), formyl (—CHO), sulphonamide ($-SO_2NR''_2$), or ketone ($-COR''$) group, in which groups R'' has the following meaning: $C_1-C_5$ alkyl, $C_1-C_5$ perfluoroalkyl, $C_5-C_{24}$ aryl, A denotes either nitrogen or carbon placed with an $R^5$ group having the meaning given above.

DETAILED DESCRIPTION OF THE INVENTION

Figure 1:
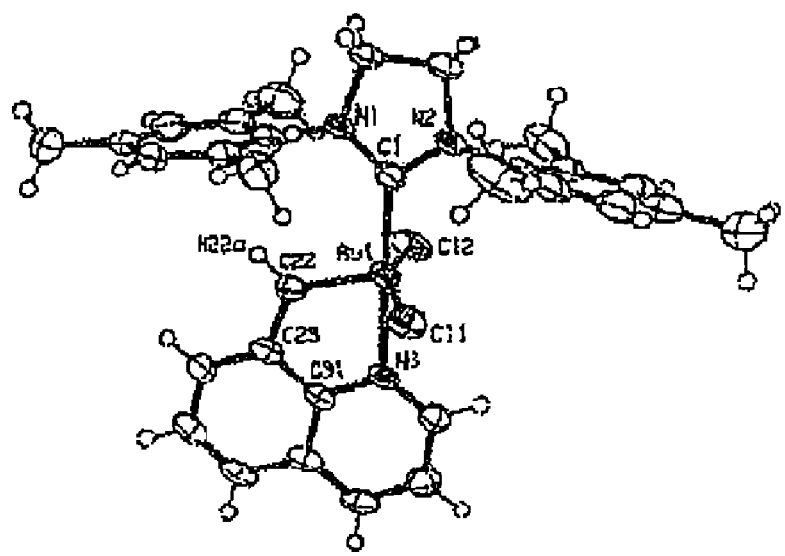
FIGS. 1 and 2: structural drawings of the compounds of formulas 10a and 10b.
Figure 2:
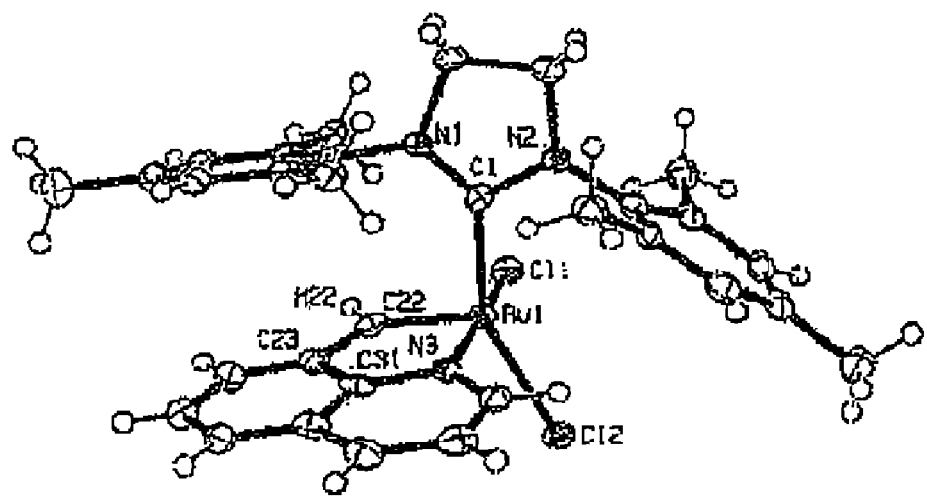

The compounds of formula 1 occur as two isomers: 1a, in which atoms X and X' are arranged trans relative to one another (see for example FIG. 1), and 1b, in which atoms X and X' are arranged cis relative to one another (see for example FIG. 2).

The method of production of the complexes of ruthenium and osmium of formula 1, in which:

M denotes ruthenium or osmium,

L denotes a neutral ligand, selected from the group comprising amines, imines, phosphines (preferably stilbines, arsines, alcohols, thiols, ethers and thioethers or the N-heterocyclic carbene ligand (NHC) represented by formula 9, where B denotes the methylene ($-C-$), 1,2-ethylene ($-C-C-$), 1,3-propenyl ($-C-C-C-$), 1,2-ethenylene ($-C=C-$) or azaethenyl ($-N=C-$) residue, unsubstituted or substituted with halogens, $C_5-C_{24}$ aryl, $C_1-C_6$ alkyl, $C_1-C_{13}$ perfluoroalkyl, $C_1-C_6$ cycloalkyl groups, moreover the alkyl groups may be joined together in a ring; preferably B denotes 1,2-ethylene ($-CH_2-CH_2-$)

R and R' denote, independently of one another, $C_5-C_{24}$ aryl, $C_5-C_{24}$ perfluoroaryl, $C_1-C_{26}$ alkyl, $C_1-C_{26}$ perfluoroalkyl, $C_1-C_7$ cycloalkyl groups, unsubstituted or substituted with halogens, $C_5-C_{24}$ aryl, $C_1-C_6$ alkyl, $C_1-C_{13}$ perfluoroalkyl, $C_1-C_6$ cycloalkyl groups, moreover the alkyl groups may be joined together in a ring, preferably R and R' denote, independently of one another, phenyl groups substituted with $C_1-C_{26}$ alkyl residues, most preferably 2,4,6-trimethylphenyl X and X' denote an anionic ligand, selected independently of one another from the group comprising anions of halogens, the phenolate anion ($C_6H_5O^-$) and perfluorophenolate anion ($C_6F_5O^-$), residues of arylcarboxylic, alkylcarboxylic, perfluoroalkylcarboxylic, alkylsulphonic, arylsulphonic, perfluoroalkylsulphonic acids, preferably chlorine $R^1$ denotes hydrogen, $C_1-C_5$ alkyl, $C_2-C_5$ alkene or $C_3-C_7$ cycloalkyl, preferably hydrogen $R^2$, $R^3$, $R^4$, $R^5$, $R^6$, $R^7$ denote, independently, $C_1-C_{25}$ alkyl, $C_1-C_{25}$ perfluoroalkyl, $C_5-C_{24}$ aryl, $C_2-C_{25}$ alkene or $C_3-C_7$ cycloalkyl, the nitro ($-NO_2$), cyano ($-CN$), carboxyl ($-COOH$), ester ($-COOR''$), sulphone ($-SO_2R''$), formyl ($-CHO$), sulphonamide ($-SO_2NR''_2$), or ketone ($-COR''$) group, in which groups R'' has the following meaning: $C_1-C_5$ alkyl, $C_1-C_5$ perfluoroalkyl, $C_5-C_{24}$ aryl, A denotes either nitrogen or carbon placed with an $R^5$ group having the meaning given above, is based according to the invention on reacting an intermediate with formula 5, in which $R^1$, $R^2$, $R^3$, $R^4$, $R^5$, $R^6$, $R^7$ and A have the meanings given above, with a carbene complex of ruthenium or osmium of formula 6, in which M denotes ruthenium or osmium, L, $L^1$ and $L^2$ denote, independently of one another, a neutral ligand selected from the group comprising amines, imines, phosphines, preferably stilbines, arsines, alcohols, thiols, ethers and thioethers or an N-heterocyclic carbene ligand (NHC) represented by formula 9, with $L^2$ optionally denoting absence of a ligand (vacancy), $R^8$ and $R^9$ denote, independently of one another, $C_5-C_{24}$ aryl groups, $C_1-C_{26}$ alkyl groups, $C_1-C_7$ cycloalkyl groups, unsubstituted or substituted with halogens, with $C_5-C_{24}$ aryl groups, with $C_1-C_6$ alkyl, $C_1-C_{13}$ perfluoroalkyl and $C_1-C_6$ cycloalkyl groups, and optionally groups $R^8$ and $R^9$ are joined together in a ring or form a fragment of an aromatic compound, preferably $R^8$ denotes hydrogen and $R^9$ denotes phenyl, X and X' have the meaning given above In the method according to the invention compounds of formula 1a and 1b are obtained as represented in Scheme II (experimental data) in a reaction between an N-heterocyclic aromatic compound with formula 5 and a complex of ruthenium or osmium with formula 6, optionally in the presence of a copper(I) salt, preferably copper(I) chloride. The reaction is carried out in chlorinated solvents, or in aliphatic, cycloaliphatic and aromatic hydrocarbons, or in mixtures thereof, preferably in methylene chloride for a time from 1 min to 250 h at a temperature from 0 to 150° C.

In addition, the pure isomer with formula 1b or a mixture of isomers with formula 1a and with formula 1b, with proportions of 1a and 1b from 100:0 to 0:100, can be obtained as a result of isomerization of a solution of compound 1a in chlorinated solvents, preferably methylene chloride, or in aliphatic, cycloaliphatic and aromatic hydrocarbons, or in mixtures thereof, for a time from 1 minute to 250 h at a temperature from 0 to 150° C.

The synthetic sequences that find general application in the production of (pre)catalysts with formula 1 are represented generally in Schemes I, III and V and as an example of synthesis of (pre)catalysts of formula 10, 11, 12, 13 in Schemes II, IV and VI-XII and XVII. These routes of synthesis are generally suitable for production of compounds with formula 1.

(Pre)catalysts of formula 1 according to the invention find application in a wide range of metathesis reactions. They make it possible to conduct reactions of ring-closure metathesis (RCM), and metathesis of the "alkene-alkyne" (ene-yne) type, but they find particular application in reactions of ring-opening metathesis polymerization (ROMP). Unexpectedly, the novel (pre)catalysts of formula 1 described here proved to be slower initiators of RCM reactions than for example the comparable known (pre)catalyst of formula 3, while retaining good properties in the polymerization reaction.

A comparative example using selected (pre)catalysts shows a slower course of initiation in the case of compounds of formula 1 (Scheme XIII). Further examples explain the use of the novel (pre)catalysts in different types of metathesis reactions: Schemes XIV-XVI.

Examples of application of the invention are presented below.

EXAMPLE I

Production of a Compound with Formula 1a Generally (Scheme I) and Particularly of Compound 10a (Scheme II)

Using a protective atmosphere of argon, a Schlenk flask was charged with a solid carbene metal complex of formula 6, in which M denotes ruthenium, X and X' denote chlorine, L denotes absence of a ligand, $L^1$ denotes tricyclohexylphosphine ($PCy_3$), $L^2$ is an NHC ligand with formula 9, in which B denotes an ethylene fragment ($-CH_2CH_2-$), R and R' denote 2,4,6-trimethylphenyl, $R^8$ hydrogen and $R^9$ phenyl (so-called Grubbs second-generation catalyst, 102 mg, 0.12 mmol), anhydrous CuCl (13 mg, 0.12 mmol), and dry deoxidized $CH_2Cl_2$ (3 ml) was added. Then a solution of compound 5 was added, in which $R^1=R^2=R^3=R^4=R^5=R^6=R^7=H$, and A denotes carbon, (20.5 mg, 0.132 mmol) in $CH_2Cl_2$ (3 ml). The suspension obtained was stirred at 40° C. for 20 min. From this moment all subsequent operations were performed in air, without the need to use the protective atmosphere of argon. The reaction mixture was concentrated in an evaporator and the material obtained was fed to a short chromatography column packed with silica gel. The column was developed using pure ethyl acetate, collecting a green fraction. After evaporating the solvent and washing the residue with a small amount of a mixture of ethyl acetate and cold n-pentane, complex 10a was obtained as a green, microcrystalline solid (62 mg, 89% yield). Rf=0.30 (ethyl acetate); $^1H$ NMR (500 MHz, $CD_2Cl_2$): 17.05 (s, 1H), 8.36 (dd, 1H, J=1.3, 3.6 Hz), 7.26-8.25 (m,4H), 7.11 (s,1H), 4.14 (s,4H), 2.46-2.51 (m,18H) ppm; $^{13}C$ NMR (125 MHz, $CD_2Cl_2$): 288.0, 212.9, 155.7, 151.7, 146.3, 139.0, 137.1, 134.0, 131.7, 129.7, 129.3, 124.6, 123.4, 116.8, 52.1, 21.3, 19.4 ppm; IR (KBr):3436, 2950, 2915, 2735, 1733, 1607, 1589, 1496, 1481, 1417, 1401, 1379, 1318, 1263, 1211, 1175, 1154, 1133, 1095, 1035, 992, 915, 850, 833, 792, 773, 748, 646, 618, 592, 578, 512, 426, 414 cm$^{-1}$; MS (ESI): 625 $[M-Cl+CH_3CN]^+$. Crystals suitable for X-ray analysis were obtained from benzene/n-hexane solution.

EXAMPLE II

Production of Compound 1b Generally (Scheme III) and Particularly of Compound 10b (Scheme IV)

Using a protective atmosphere of argon, a Schlenk flask was charged with a solid carbene complex of formula 6, in which M denotes ruthenium, X and X' denote chlorine, L denotes absence of a ligand, $L^1$ denotes tricyclohexylphosphine ($PCy_3$), $L^2$ is an NHC ligand with formula 9, in which B denotes a —$CH_2CH_2$—fragment, R and R' denote 2,4,6-trimethylphenyl, $R^8$ hydrogen and $R^9$ phenyl (so-called Grubbs second-generation catalyst, 102 mg, 0.12 mmol), and dry deoxidized $CH_2Cl_2$ (3 ml) was added. Then a solution of compound 5 was added, in which $R^1=R^2=R^3=R^4=R^5=R^6=R^7=H$, and A denotes nitrogen, (20.5 mg, 0.132 mmol) in $CH_2Cl_2$ (3 ml). The suspension obtained was stirred at 40° C. for 20 min and was then left unstirred at room temperature for 150 h. From this moment all subsequent operations were performed in air, without the need to use the protective atmosphere of argon. The reaction mixture was concentrated in an evaporator and the material obtained was fed to a short chromatography column packed with silica gel. The column was developed using pure ethyl acetate, collecting a wide green fraction. After evaporating the solvent and washing the residue with a small amount of a 1:1 mixture of $CH_2Cl_2$ and cold n-pentane, compound 10b was obtained as a dark green, microcrystalline solid (52 mg, 72% yield). IR (KBr): 3447, 2922, 2854, 2735, 1819, 1731, 1628, 1607, 1588, 1570, 1496, 1481, 1437, 1400, 1380, 1316, 1291, 1263, 1209, 1176, 1131, 1036, 987, 914, 845, 817, 796, 781, 742, 696, 639, 624, 577, 477, 453, 427 cm$^{-1}$.
$^1H$ NMR (500 MHz, $CDCl_3$) 2.90-1.40 (m, 18H), 4.30-3.60 (m, 4H), 6.15-8.05 (m, 4H), 8.14 (d, J=8.1 Hz, 1H), 8.30 (d, J=4.9 Hz, 1H), 17.44 (s, 1H) ppm. $^{13}C$ NMR (125 MHz, $CDCl_3$) 19.1, 21.2, 119.1, 123.5, 124.4, 127.6, 130.0, 133.2, 151.2, 152.8, 157.6, 217.7, 282.3 ppm. Crystals suitable for X-ray analysis were obtained from methylene chloride/n-hexane solution.

EXAMPLE III

Production of Compound 1b by Isomerization of 1a Generally (Scheme V) and Particularly of Compound 10b (Scheme VI)

Compound 10a (62 mg, 0.12 mmol) was dissolved in $CH_2Cl_2$ (1 ml). The solution was left in a dark place at room temperature for 3 days, in an argon atmosphere. After this time the solution was concentrated to dryness and washed with a mixture of solvents: ethyl acetate/n-pentane, and then methyl chloride/n-pentane. After drying, 10b was obtained as a dark green solid (48%, 30 mg). The product possesses analyses that tally with those obtained previously.

EXAMPLE IV

Production of Compound 10 as a Mixture of Isomers 10a and 10b (Scheme XVII)

Using a protective atmosphere of argon, a Schlenk flask was charged with a solid carbene complex of formula 6, in which M denotes ruthenium, X and X' denote chlorine, L denotes absence of a ligand, $L^1$ denotes tricyclohexylphosphine ($PCy_3$), $L^2$ is an NHC ligand with formula 9, in which B denotes a —$CH_2CH_2$—fragment, R and R' denote 2,4,6-trimethylphenyl, $R^8$ hydrogen and $R^9$ phenyl (so-called Grubbs second-generation catalyst, 102 mg, 0.12 mmol), anhydrous CuCl (13.1 mg, 0.132 mmol), and dry deoxidized $CH_2Cl_2$ (3 ml) was added. Then a solution of compound 5 was added, in which $R^1=R^2=R^3=R^4=R^5=R^6=R^7=H$, and A denotes carbon, (20.6 mg, 0.132 mmol) in $CH_2Cl_2$ (3 ml). The suspension obtained was stirred at 40° C. for 20 min and was then left unstirred at room temperature for 25 h. From this moment all subsequent operations were performed in air, without the need to use the protective atmosphere of argon. The reaction mixture was concentrated in an evaporator and the material obtained was fed to a short chromatography column packed with silica gel. The column was developed using pure ethyl acetate, collecting a wide green fraction. After evaporating the solvent and washing the residue with a small amount of a 1:1 mixture of $CH_2Cl_2$ and cold n-pentane, compound 10 was obtained as a mixture of isomers 10a and 10b in proportions 50/50, as a dark green, microcrystalline solid (54 mg, 72% yield). Rf=0.30 (ethyl acetate).

EXAMPLE V

Production of Compound 11a (Scheme VII)

Using a protective atmosphere of argon, a Schlenk flask was charged with a solid carbene complex of formula 6, in which M denotes ruthenium, X and X' denote chlorine, L denotes absence of a ligand, $L^1$ denotes tricyclohexylphosphine ($PCy_3$), $L^2$ is an NHC ligand with formula 9, in which B denotes a —$CH_2CH_2$—fragment, R and R' denote 2,4,6-trimethylphenyl, $R^8$ hydrogen and $R^9$ phenyl (so-called Grubbs second-generation catalyst, 101.9 mg, 0.12 mmol), anhydrous CuCl (13.1 mg, 0.12 mmol), and dry deoxidized $CH_2Cl_2$ (3 ml) was added. Then a solution of compound 5 was added, in which $R^1=R^2=R^3=R^4=R^5=R^6=R^7=H$, and A denotes nitrogen, (20.5 mg, 0.132 mmol) in $CH_2Cl_2$ (3 ml). The suspension obtained was stirred at 40° C. for 20 min.

From this moment all subsequent operations were performed in air, without the need to use the protective atmosphere of argon. The reaction mixture was concentrated in an evaporator and the material obtained was fed to a short chromatography column packed with silica gel. The column was developed using pure ethyl acetate, collecting a green fraction. After evaporating the solvent and washing the residue with a small amount of a mixture of $CH_2Cl_2$ and cold n-pentane, complex 11 was obtained as a dark green, microcrystalline solid (52 mg, 72% yield). Rf=0.30 (ethyl acetate); IR (KBr): 3439, 2953, 2920, 2855, 2735, 1943, 1730, 1630, 1607, 1574, 1484, 1420, 1379, 1264, 1202, 1149, 1080, 1035, 927, 910, 853, 834, 774, 716, 646, 578, 514, 473, 419 cm$^{-1}$; $^1$H NMR (500 MHz, CDCl$_3$) 2.38-2.50 (m, 18H), 4.16 (s, 4H), 7.08 (s, 1H), 7.35-7.62 (s, 1H), 8.38 (m, 1H), 8.45 (d, J=2.3 Hz, 1H), 8.57 (d, J=2.2 Hz, 1H), 17.00 (s, 1H) ppm. $^{13}$C NMR (125 MHz, CDCl$_3$) 19.2, 21.2, 51.7, 116.6, 124.0, 126.5, 128.6, 129.5, 134.9, 136.2, 138.5, 138.8, 141.6, 144.2, 145.6, 147.9, 155.2, 210.5, 288.2 ppm. MS (ESI): 626 [M—Cl+CH$_3$CN]$^+$.

EXAMPLE VI

Production of Compound 11a (Scheme VIII)

Using a protective atmosphere of argon, a Schlenk flask was charged with a solid carbene complex of formula 6, in which M denotes ruthenium, X and X' denote chlorine, L denotes an NHC ligand with formula 9, in which B denotes a —CH$_2$CH$_2$- fragment, R and R' denote 2,4,6-trimethylphenyl, L1 and L2 denote 3-bromopyridine, R$^8$ denotes hydrogen and R$^9$ phenyl (so-called Grubbs third-generation catalyst, 101.9 mg, 0.12 mmol), anhydrous CuCl (13.1 mg, 0.12 mmol), and dry deoxidized CH$_2$Cl$_2$ (3 ml) was added. Then a solution of compound 5 was added, in which R$^1$=R$^2$=R$^3$=R$^4$=R$^5$=R$^6$=R$^7$=H, and A denotes nitrogen, (20.5 mg, 0.132 mmol) in CH$_2$Cl$_2$ (3 ml). The suspension obtained was stirred at 40° C. for 20 min. From this moment all subsequent operations were performed in air, without the need to use the protective atmosphere of argon. The reaction mixture was concentrated in an evaporator and the material obtained was fed to a short chromatography column packed with silica gel. The column was developed using pure ethyl acetate, collecting a green fraction. After evaporating the solvent and washing the residue with a small amount of a mixture of CH$_2$Cl$_2$ and cold n-pentane, complex 11 was obtained as a dark green, microcrystalline solid (52 mg, 70% yield).

EXAMPLE VII

Production of Compound 11b (Scheme IX)

Complex 11a (trans isomer, 55 mg, 0.115 mmol) was dissolved in CH$_2$Cl$_2$ (2 ml). The solution was left in a dark place at room temperature for 3 days, in an argon atmosphere. After this time the solution was concentrated to dryness and washed with a mixture of solvents: methylene chloride/n-pentane. After drying, a dark brown solid was obtained (cis isomer, 62%, 34 mg). IR (KBr): 3436, 2921, 2855, 1942, 1725, 1630, 1593, 1483, 1442, 1404, 1379, 1314, 1266, 1219, 1195, 1154, 1079, 1034, 929, 907, 853, 823, 805, 768, 717, 667, 645, 630, 577, 474, 443, 420 cm$^1$. $^1$H NMR (200 MHz, CDCl$_3$) 1.84-2.51 (m, 18H), 4.0-4.15 (s, 4H), 7.08 (s, 4H), 7.50-7.54 (m, 2H), 7.60-7.58 (m, 1H), 8.38 (m, 1H), 8.48 (d, J=4.2 Hz, 1H), 17.30 (s, 1H) ppm.

EXAMPLE VIII

Production of Compound 1 Generally (Scheme I) and Particularly of Compound 12a (Scheme X)

Using a protective atmosphere of argon, a Schlenk flask was charged with a solid carbene complex of formula 6, in which M denotes ruthenium, X and X' denote chlorine, L denotes absence of a ligand, L$^1$ and L$^2$ denote PCy$_3$, and R$^8$ denotes hydrogen and R$^9$ phenyl (so-called Grubbs first-generation catalyst, 146.6 mg, 0.25 mmol), anhydrous CuCl (24.6 mg, 0.25 mmol), and dry deoxidized CH$_2$Cl$_2$ (5 ml) was added. Then a solution of compound 5 was added, in which R$^1$=R$^2$=R$^3$=R$^4$=R$^5$=R$^6$=R$^7$=H, and A denotes carbon, (34.1 mg, 0.23 mmol) in CH$_2$Cl$_2$ (5 ml). The suspension obtained was stirred at 35° C. for 2 min. From this moment all subsequent operations were performed in air, without the need to use the protective atmosphere of argon. The reaction mixture was concentrated in an evaporator and the material obtained was fed to a short chromatography column packed with silica gel. The column was developed using pure ethyl acetate, collecting a green fraction. After evaporating the solvent and washing the residue with a small amount of a mixture of CH$_2$Cl$_2$ and cold n-pentane, complex 12a was obtained as a pale green, microcrystalline solid (83 mg, 70% yield). Rf=0.40 (ethyl acetate).

EXAMPLE IX

Production of Compound 1 Generally (Scheme I) and Particularly of Compound 12a (Scheme XI)

Using a protective atmosphere of argon, a Schlenk flask was charged with a solid carbene complex of formula 6, in which M denotes ruthenium, X and X' denote chlorine, L denotes absence of a ligand, L$^1$ and L$^2$ denote PCy$_3$, and R$^8$ and R$^9$ denote an indenylidene residue (184.6 mg, 0.20 mmol), anhydrous CuCl (21.8 mg, 0.22 mmol), and dry deoxidized CH$_2$Cl$_2$ (5 ml) was added. Then a solution of compound 5 was added, in which R$^1$=R$^2$=R$^3$=R$^4$=R$^5$=R$^6$=R$^7$=H, and A denotes carbon, (34.1 mg, 0.22 mmol) in CH$_2$Cl$_2$ (5 ml). The suspension obtained was stirred at 35° C. for 2 min. From this moment all subsequent operations were performed in air, without the need to use the protective atmosphere of argon. The reaction mixture was concentrated in an evaporator and the material obtained was fed to a short chromatography column packed with silica gel. The column was developed using pure ethyl acetate, collecting a green fraction. After evaporating the solvent and washing the residue with a small amount of a mixture of CH$_2$Cl$_2$ and cold n-pentane, complex 12a was obtained as a pale green, microcrystalline solid (84 mg, 70% yield). Rf=0.40 (ethyl acetate).

EXAMPLE X

Production of Compound 1 Generally (Scheme I) and Particularly of Compound 13a (Scheme XII)

Using a protective atmosphere of argon, a Schlenk flask was charged with a solid carbene complex of formula 6, in which M denotes ruthenium, X and X' denote chlorine, L denotes absence of a ligand, L$^1$ denotes tricyclohexylphosphine (PCy$_3$), L$^2$ is an NHC ligand with formula 9, in which B denotes a —CH$_2$CH$_2$-fragment, R and R' denote 2,4,6-trimethylphenyl, R$^8$ hydrogen and R$^9$ phenyl (so-called Grubbs second-generation catalyst, 102 mg, 0.12 mmol), anhydrous CuCl (13 mg, 0.132 mmol), and dry deoxidized CH$_2$Cl$_2$ (3 ml) was added. Then a solution of compound 5 was added, in which R$^1$=R$^3$=R$^4$=R$^5$=R$^6$=R$^7$=H, R$^2$=CN and A denotes carbon, (20.5 mg, 0.132 mmol) in CH₂Cl₂ (3 ml). The suspension obtained was stirred at 40° C. for 20 min. From this moment all subsequent operations were performed in air, without the need to use the protective atmosphere of argon. The reaction mixture was concentrated in an evaporator and the material obtained was fed to a short chromatography column packed with silica gel. The column was developed using pure ethyl acetate, collecting a green fraction. After evaporating the solvent and washing the residue with a small amount of a mixture of ethyl acetate and cold n-pentane, complex 13a was obtained as a green, microcrystalline solid (69 mg, 89% yield). Rf=0.30 (ethyl acetate).

Examples of Applications

EXAMPLE XI

Use of Compounds 1 as Catalyst in Reactions of Ring-Closure Metathesis and ene-yne Cycloisomerization (Schemes XIII-XV)

3-cyclopentene-1,1-diethyl dicarboxylate, P1. A solution of diene S1 (84.1 mg, 0.35 mmol) in CH₂Cl₂ (15 ml) was put in a Schlenk flask, and a solution of catalyst 10a (10.8 mg, 0.018 mmol, 5 mol. %) in CH₂Cl₂ (2.5 ml) was added at a temperature of 21-23° C. It was stirred at this temperature, and samples (0.25 ml) of the reaction mixture were taken after 15 min, 30 min, 45 min, 1 h, 2 h, 4 h, 6 h, 24 h (the reaction was stopped immediately after taking the sample by adding a suitable amount of 1M ethyl-vinyl ether solution). The degree of conversion in each sample was calculated on the basis of gas chromatography (32%). Product P1 was identified by comparing with a reference standard.

In a similar reaction, (pre)catalyst 10b made it possible to obtain P1 at a yield of 14%, (pre)catalyst 11a at a yield of 38% and 11b at 18% yield.

In accordance with the data: Organometallics 2004, 23, 5399-5401, the catalyst of formula 4 catalyses, in similar reaction conditions, the formation of product P1 at a yield of 45%.

EXAMPLE XII

1-[(4-Methylphenyl)sulphonyl]-2,5-dihydro-1H-pyroline, P2. A solution of catalyst 11a (10.8 mg, 5 mol. %) in CH₂Cl₂ (2.5 ml) was added to a solution of diene S2 (84.1 mg, 0.35 mmol) in CH₂Cl₂ (15 ml). The contents of the flask were stirred at a temperature of 21-23° C. for 24 hours. The raw reaction mixture was analysed by gas chromatography. The yield of product P2 was 56%.

In a similar reaction, (pre)catalyst 10a made it possible to obtain P1 at a yield of 41%, (pre)catalyst 10b at a yield of 22% and 11b at 29% yield.

EXAMPLE XII.

2,2-Diphenyl-3-vinyl-2,5-dihydrofuran, P3. A solution of substrate S3 (86.9 mg, 0.35 mmol) in CH₂Cl₂ (3.5 ml) was put in a Schlenk flask and a solution of catalyst 10a (2.6 mg, 0.0175 mmol, 5 mol. %) in CH₂Cl₂ (3 ml) was added at a temperature of 21-23° C. It was stirred at this temperature. A sample (0.25 ml) of the reaction mixture was taken after 24 h. The degree of conversion in each sample was calculated on the basis of gas chromatography (95%). Product P1 was identified by comparing with a reference standard.

In a similar reaction, (pre)catalyst 10b made it possible to obtain P3 at a yield of 51%, (pre)catalyst 11a at a yield of 72%.

EXAMPLE XIV.

Use of Compound 10a as Catalyst in a Reaction of Ring-Opening Metathesis (Scheme XVI)

Polynorbornene P4. Norbornene (S4, 187 mg, 1.4 mmol) in CH₂Cl₂ (5 ml) was put in a flask and stirred at room temperature. Then a solution of catalyst 1 (8.7 mg, 1 mol. %) was added and the contents of the flask were stirred at the same temperature for 10 min. The flask contents were poured into another vessel containing 15 ml of methyl alcohol and a white solid was precipitated, and was separated by filtration and dried under reduced pressure using a vacuum pump. Product P4 was obtained (122 mg, 92% yield) as a white solid.

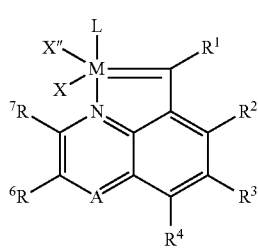

formula 1

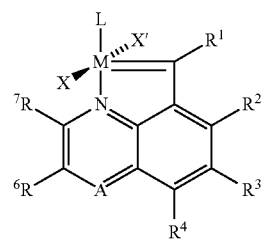

formula 1a

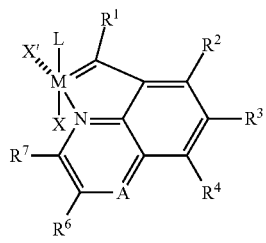

formula 1b

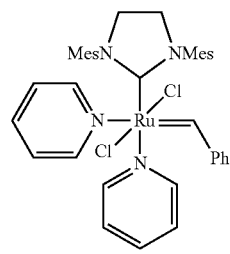

formula 2

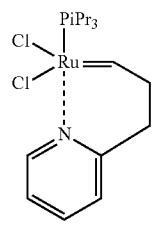
formula 3
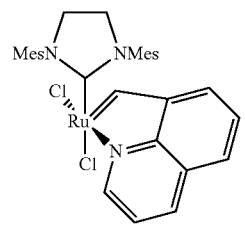
formula 10b
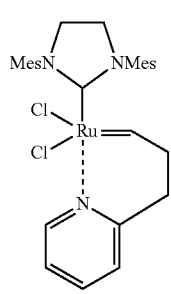
formula 4
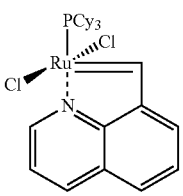
formula 12a
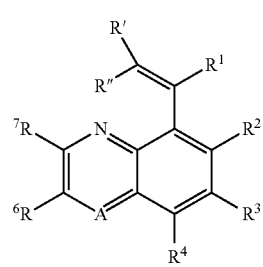
formula 5
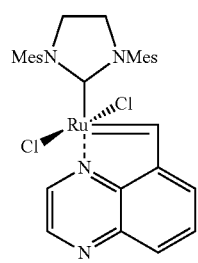
formula 11a
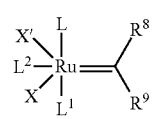
formula 6
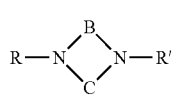
formula 9
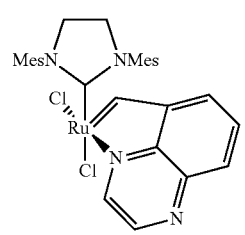
formula 11b
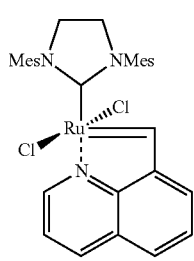
formula 10a
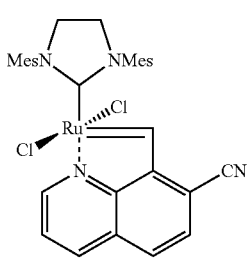
formula 13a Scheme I
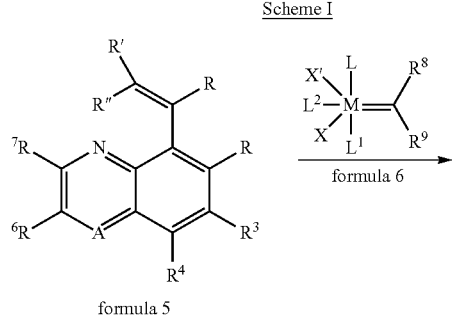
formula 5
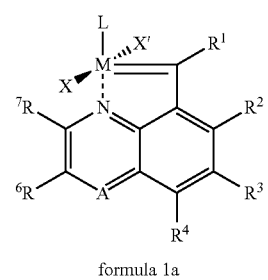
formula 6
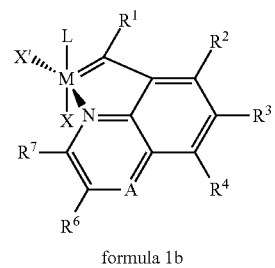
formula 1b
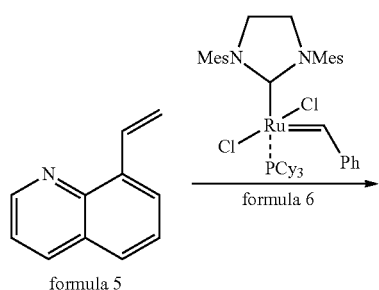
formula 1a
Scheme II
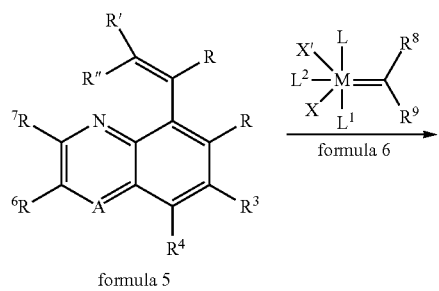
formula 6
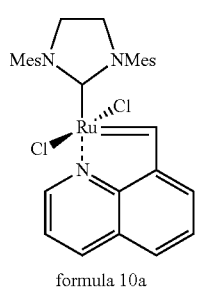
Scheme III
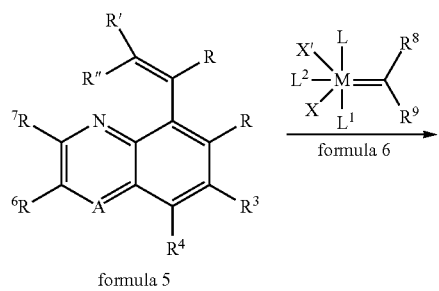
formula 5
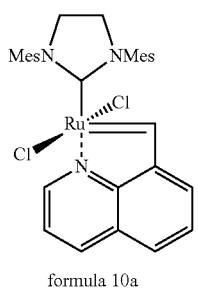
formula 6
Scheme IV
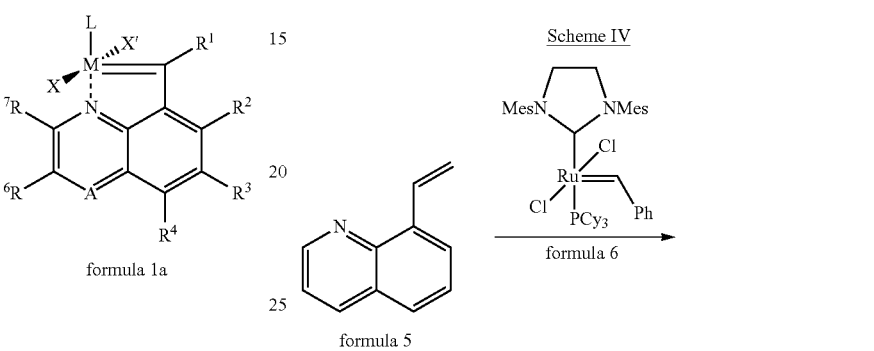
formula 5  formula 6
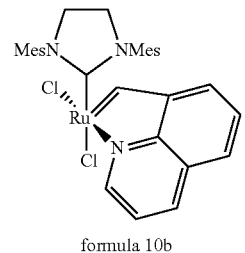
formula 10b
Scheme V
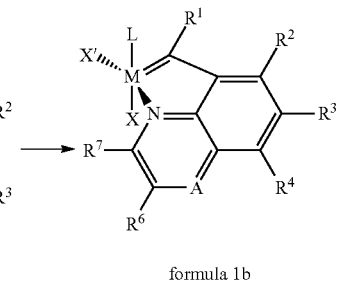
formula 1a → formula 1b
Scheme VI
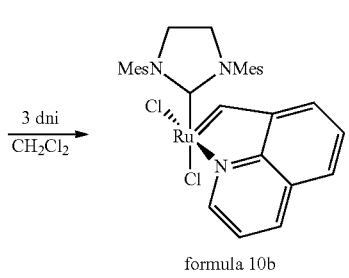
formula 10a → formula 10b
3 dni
CH₂Cl₂

Scheme VII
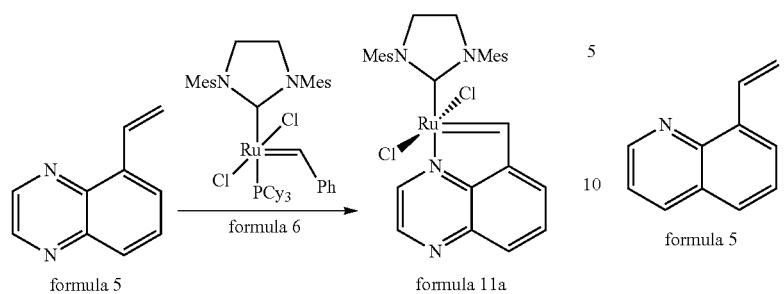
Scheme X
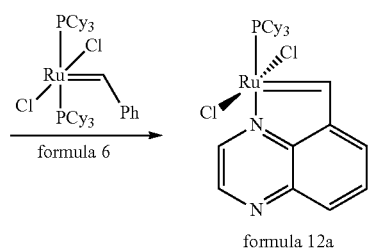
Scheme VIII
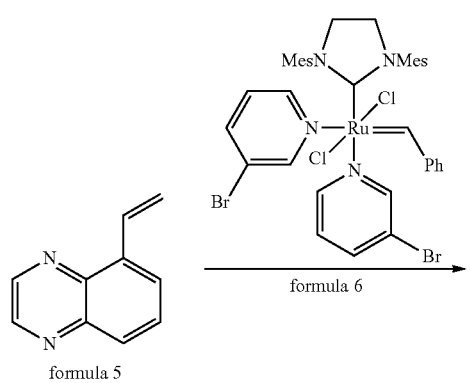
Scheme XI
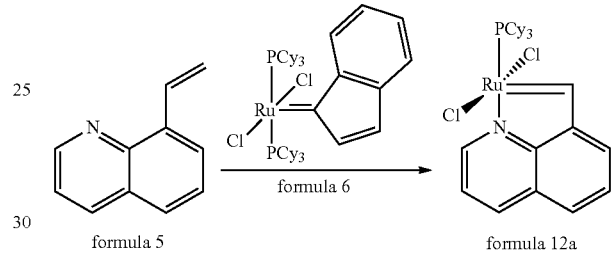
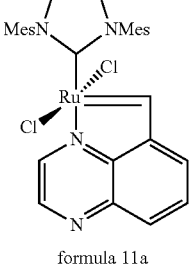
Scheme XII
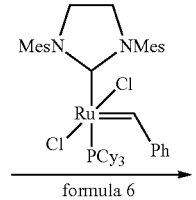
Scheme IX
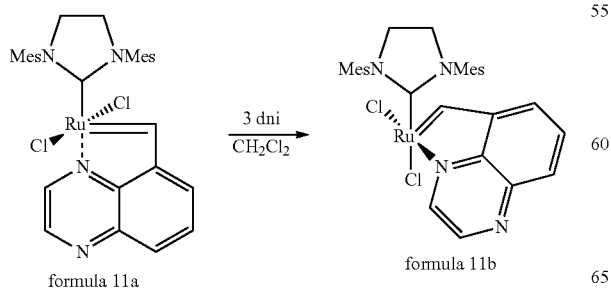

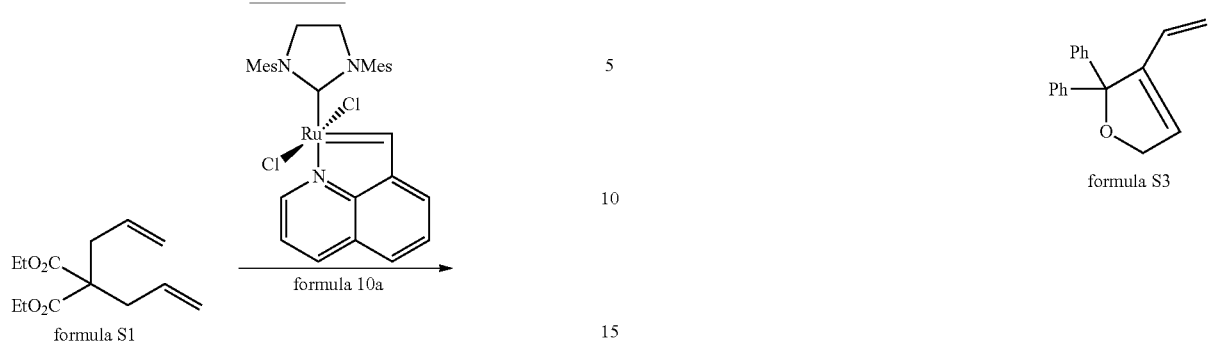
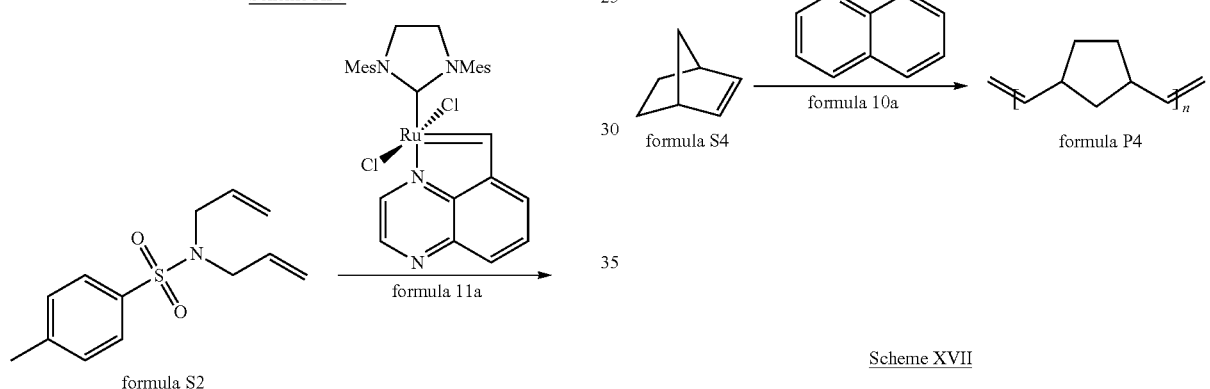
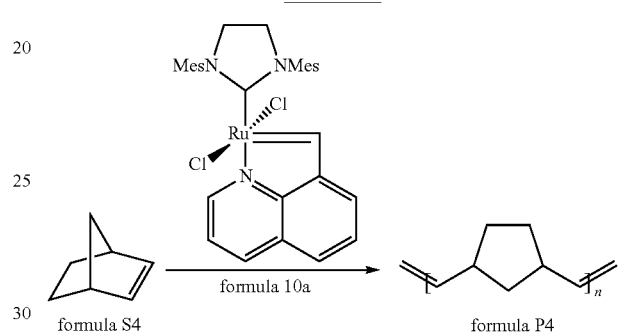
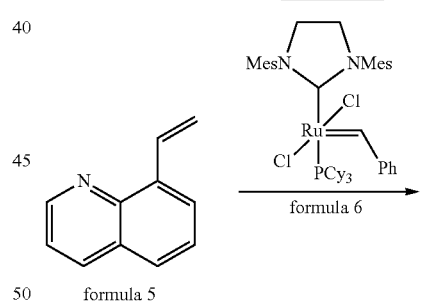
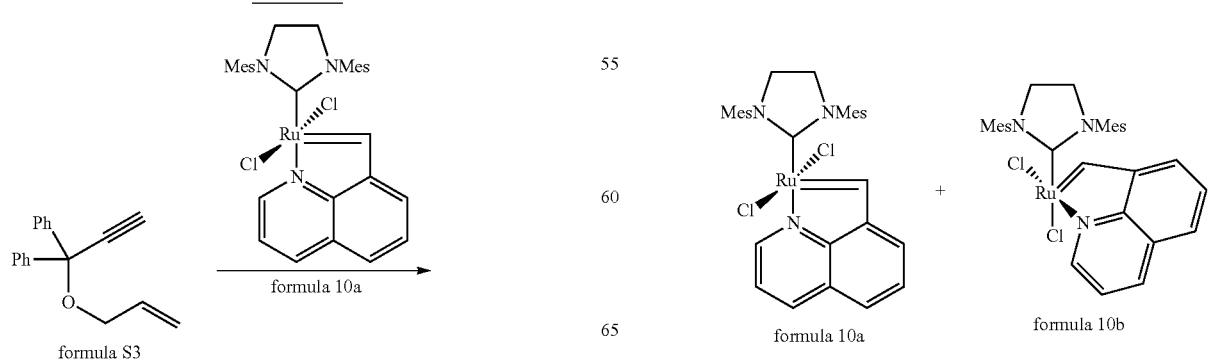

What is claimed is:

1. A complex of ruthenium represented by the formula

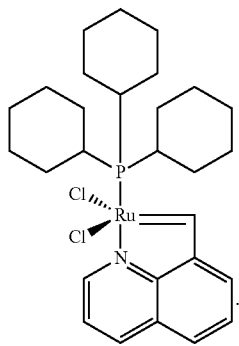

2. A method for preparing the ruthenium complex of claim 1, which comprises reacting 8- ethenylquinoline with a Ru carbene catalyst.

3. The method of claim 2, wherein the reaction is conducted in the presence of a copper(I) salt.

4. The method of claim 3, wherein the copper(I) salt is copper(I) chloride.

5. The method of claim 2, wherein the Ru carbene catalyst has the structure:

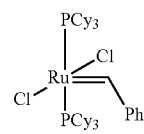

in which Ph represents a phenyl group and PCy$_3$ represents

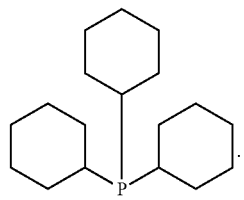

6. The method of claim 2, wherein the Ru carbene catalyst comprises an indenylidene residue.

7. The method of claim 2, wherein the reaction is performed in a chlorinated solvent, an aliphatic solvent, a cycloaliphatic solvent or an aromatic hydrocarbon solvent, or mixtures thereof.

* * * * *